United States Patent [19]

Gross

[11] Patent Number: 5,246,147

[45] Date of Patent: Sep. 21, 1993

[54] LIQUID MATERIAL DISPENSER

[75] Inventor: Joseph Gross, Moshav Mazor, Israel

[73] Assignee: Sil Medics Ltd., Petah Tikva, Israel

[21] Appl. No.: 912,430

[22] Filed: Jul. 13, 1992

[30] Foreign Application Priority Data

May 20, 1992 [IR] Iran .......................... 921613

[51] Int. Cl.[5] .............................................. B67D 5/54
[52] U.S. Cl. ...................................... 222/394; 222/396
[58] Field of Search .............. 222/351, 361, 396, 397,
222/394, 399, 400.5, 387

[56] References Cited

U.S. PATENT DOCUMENTS

| | | | |
|---|---|---|---|
| 3,199,746 | 8/1965 | Dives et al. | 222/396 |
| 3,455,485 | 7/1969 | Crownover | 222/394 |
| 3,716,171 | 2/1973 | Blomgren et al. | 222/396 |
| 4,928,850 | 5/1990 | Fallon et al. | 222/396 |
| 5,040,704 | 8/1991 | Moran | 222/394 |

Primary Examiner—David M. Mitchell
Assistant Examiner—Stephen P. Avila
Attorney, Agent, or Firm—Benjamin J. Barish

[57] ABSTRACT

A liquid material dispenser includes a housing formed with a reservoir for the liquid to be dispensed, an outlet through which the liquid is to be dispensed, and a connecting passageway between the reservoir and the outlet. A diaphgram is located in a cavity in the passageway such that one side of the diaphragm defines a pumping chamber, and the other side defines a control chamber. An electrolytic cell generates a gas to the control chamber according to the quantity of electrical current passed through the electrolyte, for driving the diaphragm through forward strokes to pump liquid to the outlet; and a slow-acting vent vents the gas from the control chamber to the atmosphere at a rate lower than that of generation of gas by the electrolytic cell, for driving the diaphragm through return strokes to refill the pumping chamber.

20 Claims, 1 Drawing Sheet

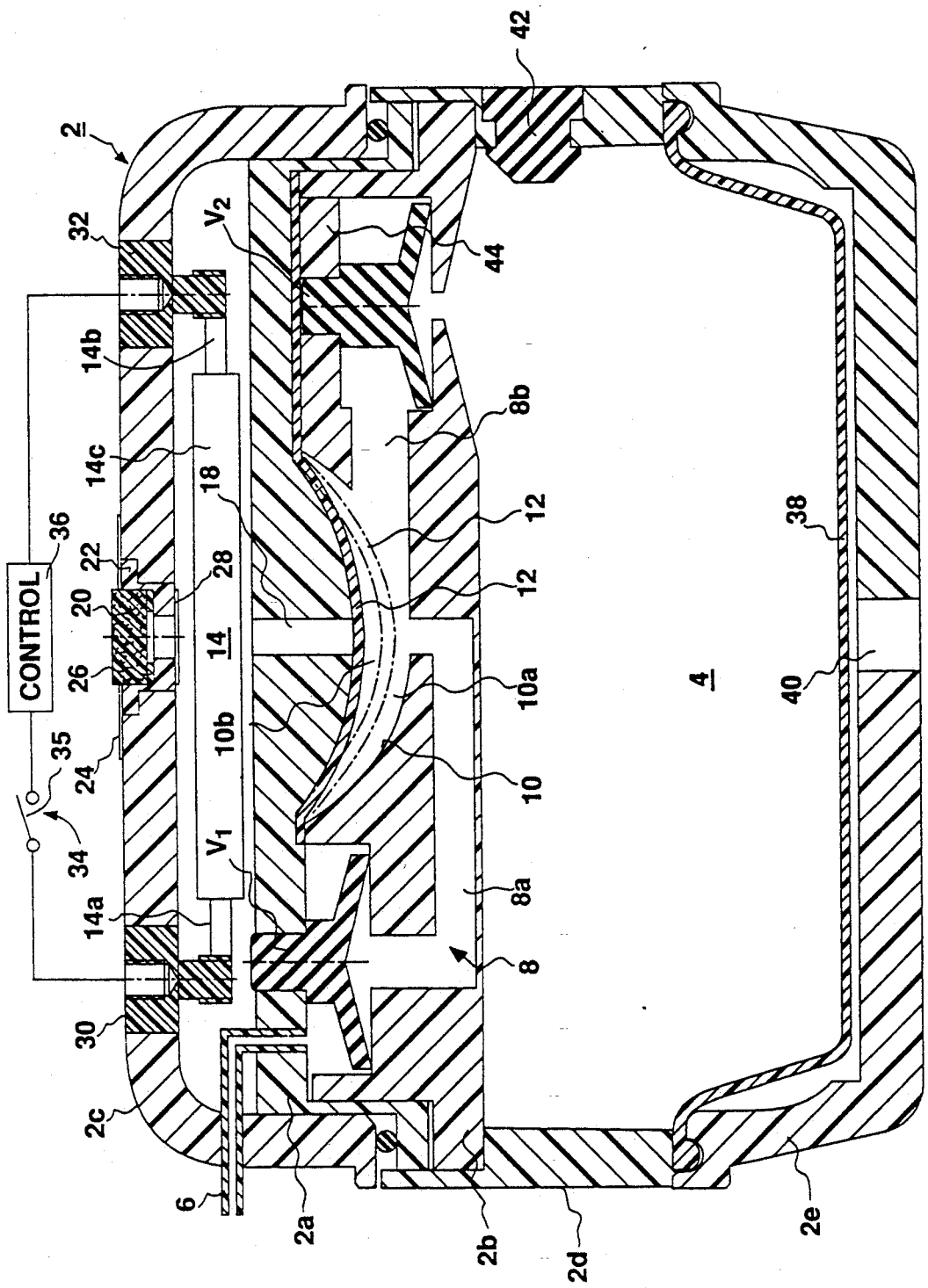

LIQUID MATERIAL DISPENSER

FIELD AND BACKGROUND OF THE INVENTION

The present invention relates to liquid material dispensers, and particularly to dispensers for dispensing medicaments at small, precisely-controlled rates. The invention is especially useful in a dispenser including an electrolytic cell generating a gas in accordance with t rate the liquid is to be dispensed, such as described in our prior U.S. Pat. Nos. 5,062,834 and 5,090,963, and it is therefore described below particularly with respect to such a dispenser.

There are many applications, such as drug delivery systems, requiring the dispensing or delivering of a liquid at a predetermined, precisely-controlled rate. Electrolytic pumps, such as described in our above U.S. patents, have been developed for this purpose. These pumps, however, generally include relatively large pumping chambers, and therefore their pumping rates may be significantly influenced by pressure and temperature changes particularly when the dispenser is used over long periods of time and/or under varying ambient conditions.

It would therefore be desirable to provide a liquid material dispenser or pump of a construction which may include a pumping chamber of relatively small volume so that the rate of delivery of the liquid is less sensitive to pressure and temperature changes.

OBJECTS AND BRIEF SUMMARY OF THE INVENTION

According to the present invention, there is provided a liquid material dispenser, comprising: a housing including a reservoir for liquid to be dispensed, an outlet through which the liquid is dispensed, and a connecting passageway between the reservoir and the outlet; and a reciprocatable pumping member in the passageway such that one side of the pumping member defines a pumping chamber with the passageway, and the other side defines a pressure-control chamber. The pumping member is cyclically displaceable through forward and return strokes for pumping liquid from the reservoir to the outlet. Valve means in the passageway are effective, during one of the strokes, to cause the pumping member to draw liquid from the reservoir into the pumping chamber, and during the other of the strokes, to cause the pumping member to pump liquid from the pumping chamber through the outlet. Feeding means feeds a gas at a preselected time and rate to the pressure-control chamber to drive the pumping member through one of the strokes; and a slow-acting vent vents the gas from the pressure-control chamber continuously at a rate lower than the gas feeding rate, to drive the pumping member through the other of the strokes.

According to a further feature in the preferred embodiment of the invention described below, the feeding means comprises an electrolytic cell including electrodes and an electrolyte which generates a gas according to the quantity of the electrical current passed through the electrolyte. According to a still further feature, the slow-acting vent comprises a gas-permeable porous member. The latter member may be of sintered metal or sintered plastic.

As will be described more particularly below, such a dispenser may be operated by closing an electrical circuit to the electrolytic cell to cause gas to be generated at a predetermined rate and during a predetermined time period, e.g., one minute, and then interrupting the current supplied to the electrolytic cell for a longer interval, e.g., four minutes. Thus, during the one-minute interval, gas will be generated to drive the pumping member (e.g., a diaphragm) through a forward stroke to pump liquid from the pumping chamber through the outlet; and during the subsequent four-minute interval when no gas is generated, the slow-acting vent vents the gas from the pressure-control chamber to the atmosphere to thereby drive the pumping member through the return stroke to draw liquid from the reservoir to the pumping chamber.

In such a construction, the pumping chamber may be of a relatively small volume so that the dispenser is much less sensitive to temperature and pressure fluctuations, and therefore can more precisely control the delivery of the liquid. This is particularly important when very low delivery rates are involved such as in the administration of medicaments to a patient.

Further features and advantages of the invention will be apparent from the description below.

DESCRIPTION OF A PREFERRED EMBODIMENT

The invention is herein described, by way of example only, with reference to the accompanying single drawing figure illustrating a preferred embodiment of the invention.

The illustrated preferred embodiment is a liquid material dispenser for delivering drugs at a slow, controlled and precise rate, to a patient. It includes an electrolytic cell, such as described in our prior U.S. Pat. Nos. 5,062,834 and 5,090,963, for controlling the rate and time of delivery of the drug to the patient.

The illustrated liquid material dispenser includes a housing, generally designated 2, having a reservoir 4 for the liquid to be dispensed, an outlet 6 through which the liquid is dispensed, and a connecting passageway 8 between the reservoir and the outlet. Passageway 8 includes an enlarged cavity 10 occupied by a diaphragm 12.

Diaphragm 12 serves as a reciprocatable pumping member and is cyclically displaceable through forward and return strokes for pumping liquid from reservoir 4 through the outlet 6. The cyclical reciprocation of diaphragm 12 is effected by an electrolytic cell, generally designated 14, within a compartment 16 in housing 2 and communicating with cavity 10 at one side of the diaphragm via a bore 18. It will thus be seen that the diaphragm defines a pumping chamber 10a on one side for pumping liquid from 4 through the outlet 6, and a pressure-control chamber 10b on the opposite side, communicating via bore 18 with electrolytic cell 14 in compartment 16.

Two one-way umbrella valves $V_1$, $V_2$ are in the connecting passageway between reservoir 4 and outlet 6. Valve $V_1$ is proximal to the outlet 6, i.e., between it and pumping chamber 10a, and is oriented such that during the forward strokes of diaphragm 12, the diaphragm pumps liquid from the pumping chamber 10a through the outlet 6 via section 8a of the connecting passageway 8. Valve $V_2$ is located proximal to the reservoir 4, i.e., between it and pumping chamber 10a, and is oriented such that during the return strokes of the diaphragm 12, it permits the diaphragm to draw liquid from the reservoir 4 into the pumping chamber 10a via section 8b of the connecting passageway 8.

As will be described more particularly below, the electrolytic cell 14 in compartment 26 is electrically controlled to generate a gas at a preselected time and at a preselected rate and to feed the gas to the pressure-control chamber 10b acting on diaphragm 12, to drive the diaphragm through its forward strokes for pumping liquid from the pumping chamber 10a to the outlet 6 via valve $V_1$. The illustrated dispenser further includes a slow-acting vent 20 for venting the gas from the pressure-control chamber 10b to the atmosphere continuously, and at a rate lower than the gas feeding rate, to drive the diaphragm through the return strokes, and thereby to draw liquid from reservoir 4 into the pumping chamber 10a.

The slow-acting vent 20 is in the form of a gas-permeable porous cap. It may be of sintered metal particles, such as of steel, copper, aluminum, titanium, etc.; alternatively, it may be of sintered plastic particles, such as of polypropylene or polytetrafluorethylene, such as "Teflon" (Reg.T.M.).

The gas-permeable cap 20 is received within an apertured seat, e.g., of plastic material, fixed to housing 2 and is retained in the seat by any suitable means, such as by a plastic clip 24. An O-ring 26 is interposed between cap 20 and the outer face of seat 22. The inner face of seat 22 carries a hydrophobic membrane 28 which is permeable to gas but not to liquid, to thereby prevent the electrolyte 14 from clogging the cap.

The electrolytic cell 14, located within compartment 16 communicating with the pressure-control chamber 10b on one side of diaphragm 12, may be of any known construction, such as described in our prior U.S. Pat. Nos. 5,062,834 and 5,090,963. Basically, it includes a pair of electrodes 14a, 14b, and an electrolyte 14c which generates a gas according to the quantity of electrical current passed through the electrolyte. The two electrodes 14a, 14b are connected to terminals 30, 32 for connection to an external electrical control circuit 34. As known in such electrolytic-type pumps, the electrical circuit control 34 includes electrical switching means 35 for controlling the time at which electrical current is applied to the electrolytic cell 14, and also current-control means 36 for controlling the magnitude of the applied electrical current, and thereby the rate of generation of the gas by the electrolytic cell.

Housing 2, reservoir 4, and/or diaphragm 12, may be of any suitable configuration, e.g., circular or rectangular in cross-section.

For ease in assembly and disassembly of the illustrated dispenser, housing 2 is made of a plurality of sections, namely: a first section 2a; a second section 2b clamping diaphragm 12 between it and section 2a; a third section 2c defining, with section 2a, the pressure-control chamber 10b on one side of diaphragm 12 and including the electrolytic cell compartment 16; a fourth section 2d secured at one end to housing sections 2a, 2b and 2c; and a fifth section 2c secured to the opposite end of housing section 2d. A rolling diaphragm 38 is clamped between the two sections 2d, 2e; and an air vent opening 40 is formed in housing section 2e.

It will thus be seen that the reservoir 4 is defined by housing section 2d and the rolling diaphragm 38. Housing section 2d carries an injection plug 42 for filling the reservoir by injection via a syringe needle, as well known. Diaphragm 38 and vent opening 40 permit reservoir 4 to expand and contract according to the quantity of the liquid material contained in the reservoir.

The base of one-way umbrella valve $V_1$ is secured in an opening formed in housing section 2a; and the base of one-way umbrella valve $V_2$ is secured in an opening formed in a rigid plastic member 44 between housing sections 2b and 2a.

The illustrated dispenser operates in the following manner:

Reservoir 4 is filled by a syringe piercing the injection plug 42 until the injected liquid drug begins to exit from the outlet 6. When this occurs, not only is the reservoir 4 completely filled with the liquid drug, but also the connecting passageway 8 and the cavity 10 are filled with the drug up to the outlet 6.

The time and rate of delivery of the drug from reservoir 4 to the outlet 6 are controlled by the electrical control circuit 34 for energizing the electrolytic cell 14 via its electrodes 14a, 14b and their electrical terminals 30, 32. As one example, the electrical control circuit 30 may be such so as to energize the two electrodes 14a, 14b at periods of one minute followed by intervals of four minutes. During the one-minute interval when the electrodes 14a, 14b are energized, the electrolyte 14 generates a gas which is fed via bore 18 to the pressure-control chamber 10b at one side of diaphragm 12. This gas displaces the diaphragm, as shown in broken lines at 12' in the drawing, thereby stressing the diaphragm to contract the pumping chamber 10a. This contraction of the pumping chamber applies a pressure via section 8b of the connecting passageway 8 to close valve $V_2$, and also applies a pressure via section 8a of the connecting passageway to open valve $V_1$. Accordingly, liquid from pumping chamber 10a is pumped via valve $V_1$ through the outlet 6 for the one-minute period during which the electrolytic cell 14 is energized, and at a rate corresponding to the magnitude of electrical current passed through the electrolyte.

The pressure-control chamber 10b is continuously vented to the atmosphere via the gas-permeable porous cap 20. Since the rate of venting of the gas is less than the rate of generation of the gas by the electrolytic cell 14, this venting of the gas does not substantially influence the dispenser during the pumping stroke. However, as soon as the pumping stroke is completed by the termination of the electrical current applied to the electroytic cell 14 (e.g., after one minute), the venting of the gas via cap 20 to the atmosphere slowly reduces the pressure in chamber 10b so that the stressed diaphragm 12 tends to move back to its initial condition (shown in full lines in the drawing), thereby expanding the pumping chamber 10a. This expansion of the pumping chamber lowers the pressure in passageway section 8a to close valve $V_1$; it also lowers the pressure in passageway section 8b to open valve $V_2$ and to draw liquid from reservoir 4 into the pumping chamber 10a.

Thus, at the end of the interval (e.g., four minutes) following the termination of the electical current applied to the electrolytic cell 14, diaphragm 12 will have been returned to its home positiion (shown in full lines in the drawing), and pumping chamber 10a will have been refilled with liquid from reservoir 4. When electrical current is again applied to the electrolytic cell 14 to generate additional gas, the diaphragm 12 will again be driven through a forward pumping stroke for pumping the liquid within pumping chamber 10a via valve $V_1$ through the outlet 6.

It will be appreciated that the illustrated dispenser does not hold large volumes of gases over extended periods, and therefore is not significantly sensitive to temperature and pressure fluctuations. The illustrated dispenser may therefore be used for dispensing liquids at precisely-controlled rates and over long periods of time between refillings.

While the invention has been described with respect to one preferred embodiment, it will be appreciated that many other variations, modifications and applications of the invention may be made.

What is claimed is:

1. A liquid material dispenser, comprising:
   a housing including a reservoir for liquid to be dispensed, an outlet through which the liquid is dispensed, and a connecting passageway between said reservoir and said outlet;
   a reciprocatable pumping member in the passageway, such that one side of the pumping member defines a pumping chamber with the passageway, and another side defines a pressure-control chamber, said pumping member being cyclically displaceable through forward and return strokes for pumping liquid from said reservoir to said outlet;
   valve means in said passageway effective, during one of said strokes, to cause the pumping member to draw liquid from said reservoir into said pumping chamber, and during the other of said strokes, to cause the pumping member to pump liquid from said pumping chamber through said outlet;
   feeding means for feeding a gas at a preselected time and rate to said pressure-control chamber to drive the pumping member through one of said strokes; and
   a slow-acting vent for venting the gas from said pressure-control chamber continuously at a rate lower than said gas feeding rate, to drive the pumping member through the other of said strokes.

2. The dispenser according to claim 1, wherein said feeding means comprises an electrolytic cell including electrodes and an electrolyte which generates a gas according to the quantity of electrical current passed through said electrolyte.

3. The dispenser according to claim 1, wherein said slow-acting vent comprises a gas-permeable porous member.

4. The dispenser according to claim 3, wherein said gas-permeable porous member is of sintered metal.

5. The dispenser according to claim 3, wherein said gas-permeable porous member is of sintered plastic.

6. The dispenser according to claim 3, wherein there is a hydrophobic membrane between said presssure-control chamber and said gas-permeable porous member.

7. The dispenser according to claim 6, wherein said gas-permeable porous member is in the form of a cap mounted on an apertured seat fixed to the housing, with an O-ring disposed between the cap and one side of the seat, said hydrophobic membrane being disposed between the other side of the seat and the pressure-control chamber.

8. The dispenser according to claim 1, wherein said pumping member is a diaphragm.

9. The dispenser according to claim 8, wherein said feeding means includes an electrolytic cell communicating with said pressure-control chamber, said electrolytic cell including electrodes and an electrolyte which generates a gas according to the quantity of electrical current passed through said electrolyte.

10. The dispenser according to claim 9, wherein said housing includes at least three sections, said diaphragm being clamped between first and second housing sections, said pressure-control chamber being defined by said first section and a third section, said first section being formed with a passageway leading to said diaphragm.

11. The dispenser according to claim 10, wherein said housing includes a fourth section and a fifth section, said fourth section being secured to said second section, and said fifth section being secured to said fourth section with a second diaphrgam therebetween, said reservoir being defined by said fourth section and said second diaphragm, said fifth section including a venting opening and defining a venting chamber with said second diaphragm.

12. The dispenser according to claim 1, wherein said valve means comprises:
   a first one-way valve in said passageway proximal to said outlet and oriented such that during one of said strokes the pumping member pumps liquid from said pumping chamber through said outlet; and
   a second one-way valve in said passageway proximal to said reservoir and oriented such that during the other of said strokes the pumping member draws liquid from said reservoir to said pumping chamber.

13. The dispenser according to claim 12, wherein said first and second valves are umbrella valves cooperable with valve openings formed in said housing.

14. A liquid material dispenser, comprising:
   a housing including a reservoir for liquid to be dispensed, an outlet through which the liquid is to be dispensed, and a connecting passageway between said reservoir and said outlet;
   a diaphrgam in the passageway such that one side of the diaphragm defines a pumping chamber, and another side defines a pressure-control chamber;
   an electrolytic cell communicating with said control chamber and including electrodes and an electrolyte which generates a gas according to the quantity of electrical current passed through said electrolyte, for driving said diaphragm through forward strokes;
   a slow-acting vent for venting the gas from said pressure-control chamber at a rate lower than that of generation of gas by said electrolytic cell, for driving the diaphragm through return strokes; and
   valve means in said passageway causing the diaphragm to pump liquid from said pumping chamber through said outlet during said forward strokes, and to draw liquid from said resrvoir into said pumping chamber during said return strokes.

15. The dispenser according to claim 14, wherein said slot-acting vent comprises a gas-permeable porous member.

16. The dispenser according to claim 15, wherein said gas-permeable porous member is of sintered metal.

17. The dispenser according to claim 15, wherein said gas-permeable porous member is of sintered plastic.

18. The dispenser according to claim 15, wherein there is a hydrophobic membrane between said pressure-control chamber and said gas-permeable porous member.

19. The dispenser according to claim 15, wherein said gas-permeable porous member is in the form of a cap mounted on an apertured seat fixed to the housing, with an O-ring disposed between the cap and one side of the seat, said hydrophobic membrane being disposed between the other side of the seat and the pressure-control chamber.

20. The dispenser according to claim 15, wherein said housing includes at least three sections, said diaphragm being clamped between first and second housing sections, said pressure-control chamber being defined by said first section and a third section, said first section being formed with a passageway leading to said diaphragm.

* * * * *

UNITED STATES PATENT AND TRADEMARK OFFICE
CERTIFICATE OF CORRECTION

PATENT NO. : 5,246,147
DATED : September 21, 1993
INVENTOR(S) : Joseph Gross

It is certified that error appears in the above-indentified patent and that said Letters Patent is hereby corrected as shown below:

On the cover page:  Under Foreign Application Priority Data, change "Iran" to --Ireland--.

Column 1:  Line 11, at end of line, change "t" to --the--.

Column 2:  Line 53, after "from" insert --the reservoir--.

Signed and Sealed this

Twenty-first Day of February, 1995

Attest:

BRUCE LEHMAN

Attesting Officer

Commissioner of Patents and Trademarks